(12) United States Patent
Cislo

(10) Patent No.: US 8,454,159 B1
(45) Date of Patent: Jun. 4, 2013

(54) METHOD AND DEVICES FOR TREATMENT OF MACULAR DEGENERATION VISUAL IMPAIRMENT

(76) Inventor: Donald M. Cislo, Malibu, CA (US)

( * ) Notice: Subject to any disclaimer, the term of this patent is extended or adjusted under 35 U.S.C. 154(b) by 0 days.

(21) Appl. No.: 13/478,693

(22) Filed: May 23, 2012

(51) Int. Cl.
*G02C 7/02* (2006.01)
*G02C 7/16* (2006.01)

(52) U.S. Cl.
USPC .................... 351/159.63; 351/159.78; 351/57

(58) Field of Classification Search
USPC .............. 351/159.16, 159.52, 159.63, 159.78
See application file for complete search history.

(56) References Cited

U.S. PATENT DOCUMENTS

| | | | |
|---|---|---|---|
| 3,010,364 A | 11/1961 | Lindblom | |
| 6,139,145 A | 10/2000 | Israel | |
| 6,146,366 A | 11/2000 | Schachar | |
| 6,299,304 B1 | 10/2001 | Demuth | |
| 6,582,073 B1 * | 6/2003 | Hayes et al. | 351/45 |
| 7,374,284 B2 | 5/2008 | Peli | |
| 7,488,069 B2 | 2/2009 | Hull | |
| 7,588,333 B2 | 9/2009 | Dreher | |
| 2003/0065020 A1 | 4/2003 | Gale et al. | |
| 2003/0187502 A1 * | 10/2003 | Lipshitz | 623/6.11 |

* cited by examiner

*Primary Examiner* — Scott J Sugarman
(74) *Attorney, Agent, or Firm* — Cislo & Thomas, LLP

(57) ABSTRACT

A method and device for improving the perceived vision of a person having macular degeneration wherein, a plurality of means is employed to selectively block the reception of a distorted image caused by the impaired eye whereby overall vision is improved.

3 Claims, 2 Drawing Sheets

METHOD AND DEVICES FOR TREATMENT OF MACULAR DEGENERATION VISUAL IMPAIRMENT

BACKGROUND OF THE INVENTION

1. Technical Field

The invention is directed to method and apparatus for correcting, or ameliorating vision defects associated with central field vision loss such as usually formed and a result of wet macular degeneration. The invention utilizes relatively low cost devices and a method of use that helps to diminish eye vision distortion and eye strain where at least one eye of an individual is affected with the central vision loss normally associated with macular degeneration, especially of the wet variety.

2. Background Art

The retina of the eye has essentially two parts, for description of the invention: the macula and peripheral retina. The macula is very small and is generally located in the center of the retina. The area surrounding the macula is the peripheral retina and makes up 95% of the retina.

The macula is necessary for normal central vision acuity and consists mostly of light-sensitive cells called cones. In macular degeneration, the light-sensitive cells are damaged and, thus, inoperative. Common causes of macular degeneration are age, diabetic retinopathy, ocular vascular accidents or diseases, retinal dystrophies, central nervous system diseases, etc. The inoperative macula can create a very dim and blurred central spot in the vision field, called a scotoma, and the rest of the vision field can become dimmer than normal, and impaired, believed to be caused by a distorted image being transmitted to the brain along with an un distorted image. The severity of the loss depends on the progression of the disease. In macular degeneration, central vision may be reduced or completely lost making it difficult to read, watch television, drive, sew, etc.; because of the reception of a distorted visual along with an undistorted visual where only one eye is affected thereby producing an off set, ghost or similar distorted overall image to the affected individual.

The peripheral retina provides side or peripheral vision for orientation in space and consists mostly of light sensitive cells called rods. The rods are more sensitive to light and motion than cones. The other, peripheral part of the retina typically remains un-diseased and intact in persons with macular degeneration.

Surgical procedures, such as laser photocoagulation and photodynamic therapy, and therapeutic treatments, such as supplements or pharmaceutical agents have had mixed and negative results for treatments of macular degeneration.

Therefore, a need exists for a vision enhancing method and device for persons with macular degeneration that can block distorted images away from the optic axis so as to improve overall vision with respect to the affected and unaffected eye.

BRIEF SUMMARY OF INVENTION

An embodiment of the invention involves a method of determining optimum vision wherein at least one eye of an individual is affected with wet macular degeneration such that the individual is cognizant of perceived images that are out of register, distorted or otherwise affected.

Another application of the invention involves the provision of partial image blocking coincident with the usual central vision loss associated with macular degeneration so as to provide reduced overall vision distortion, and thus less eye strain and unimpaired vision in conjunction with the unaffected eye.

Further embodiments of the invention utilize the application of partial vision blocking members to reduce eye strain, double vision and other effects due to the formation of central blood pooling and or blood vessels in an affected wet macular degeneration eye.

To establish the best visual for the viewer, the methodology is to determine the light or vision blocking amount and placement with respect to the affected eye, which is achieved through a low cost trial and error procedure, using relatively inexpensive means.

Another embodiment of the invention utilizes one of a plurality of partial vision blocking means of various sizes, shapes and colors utilizing low cost devices and materials to obtain the best possible overall vision performance during one of several, available medical treatments of the affected eye or eyes.

Further embodiments will become apparent as the description proceeds herein.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. However, it is to be understood that other applications of the method and devices of the invention will be readily apparent to those of ordinary skill in the art.

Figure 1:
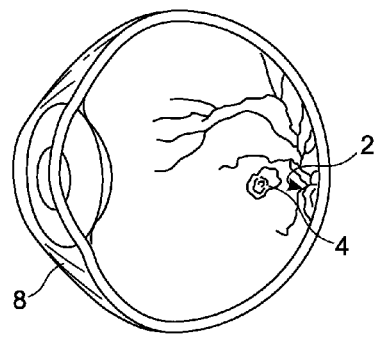
FIG. 1 schematically depicts a human eye illustrating the important components making up the human eye.

Referring to the drawings wherein like numbers of reference refer to like elements throughout, FIG. 1 depicts the schematic showing of a typical eye wherein a wet macular degeneration condition is shown.

In this condition a pool of blood, or group of blood vessels 2 has formed on the macula 4, and most usually in the center thereof by reason of some of the blood vessels 2 having leaked or formed thereby obscuring, hindering and otherwise preventing the correct reception of light projections through the eye 8 for correct registration of the images from both eyes upon the optic nerve, not shown, for recognition by the brain.

Figure 8:
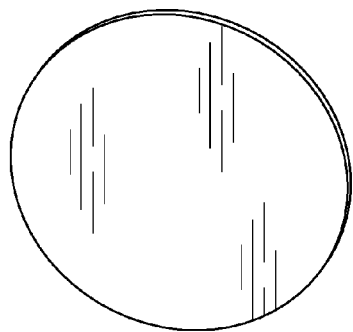
FIG. 8 illustrates a total vision blocking device that may be used in the practice of the invention.
Figure 9:
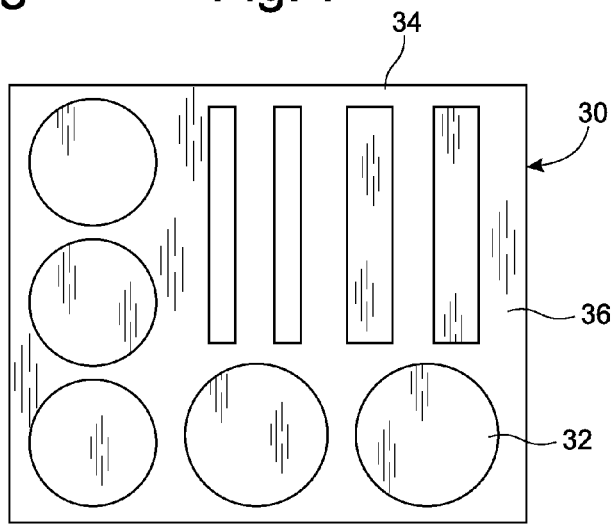
FIG. 9 illustrates still another embodiment of the invention comprising various sized and colored partial vision blocking members for practicing the invention.

To correct eye strain, distortion or improper registration due to the presence of blood vessels 2, there is provided means to prevent the projection of the distorted or malformed image. Assuming only one eye is affected by, for example, the wet macular degeneration condition, a full eye patch may be used to cover the affected eye to thereby eliminate the distorted image. Alternatively, when the affected person wears glasses, prescription or otherwise, a fully, opaque covering may be placed over the lens of the effected eye to thereby eliminate the distorted image from interfering with the wearer's vision. An opaque patch, blank or other vision blocking member as shown in FIG. 8 having an adhesive backing may be used for this purpose. Other means of attaching an eye patch on other vision blocking members will make themselves readily obvious.

However, a preferred methodology, where complete blocking of the attached eye, and thus distorted image is not desired, an alternative is shown in FIGS. 2-7 and 9 inclusive.

A variety of distorted image blocking expedients are contemplated by the herein disclosed invention.

Figure 2:
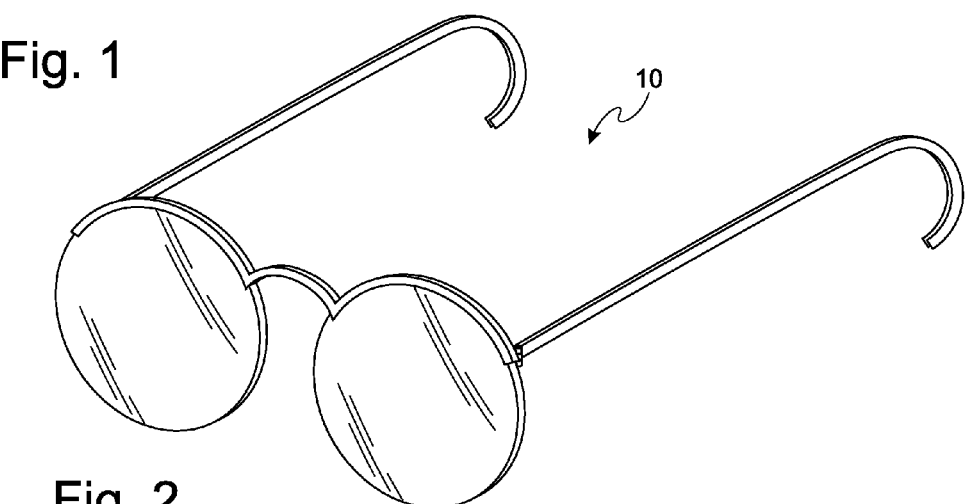
FIG. 2 illustrates a conventional pair of eyeglasses, prescription or non-prescription with which the various embodiments of the invention may be used.
Figure 3:
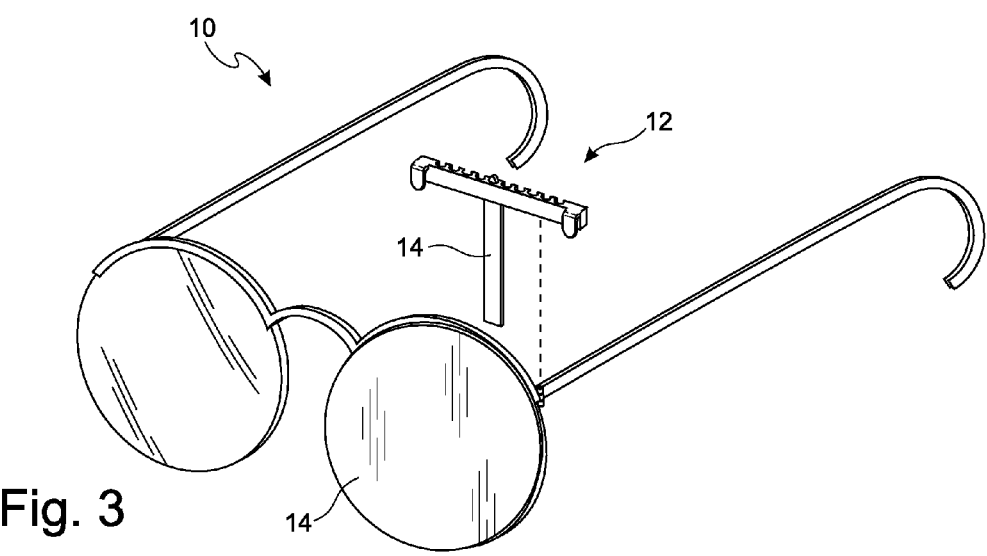
FIG. 3 illustrates one embodiment of the devices of the invention in association with a pair of eyeglasses.
Figure 4:
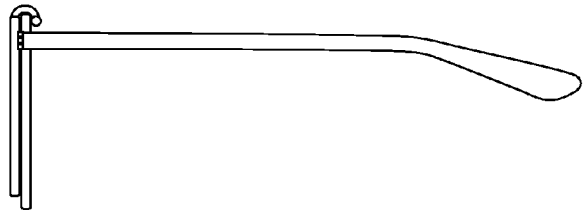
FIG. 4 Illustrates how another view of one of the devices of the invention associated with a pair of eyeglasses.
Figure 5:
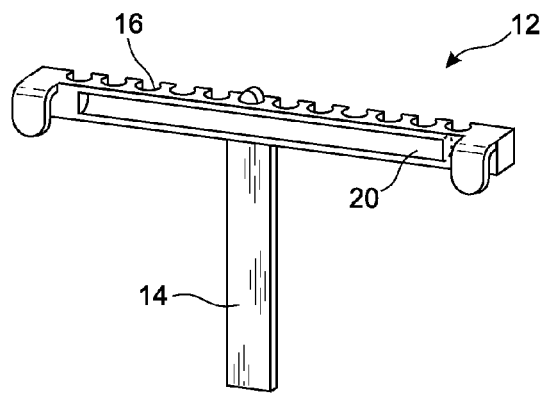
FIG. 5 is an enlarged view of part of the structure utilized to practice the invention.

As shown in FIGS. 2-4, a typical pair of glasses 10 is shown, prescription or otherwise. As contemplated by the invention, most effective application of the proposed alternatives are best achieved when only one eye has the macular degenerative condition. However, it is contemplated that partial blocking, as opposed to full blocking of the distorted image for both affected eyes would improve vision, lessen eye strain, and improve elimination of vision distortion.

Thus, application of the invention will be described with respect to only one eye being affected, it being understood that one of the ordinary skill in the art would recognize its application of the invention when both eyes are impaired and only partial vision blocking is possible.

The eye glasses 10 are fitted with clip member 12 of the clip-on type normally found in the market place having lens adhering clips 13 but having a positionable, depending, vertical member 14 of sufficient length to cover the lens's 15 vertical length.

The clip member 12 may alternatively have a slide channel 20 for receiving abutment 22 positioned at right angles to depending, vertical member 24 (FIG. 7) for sliding, friction fit engagement with slide channel 20 and for maximum, selective positioning as will be more fully explained, it only being necessary for the user to move, slide or position the depending vertical member 24 to best block out the distorted image so as to permit the user to have improved, relatively eye strain-less viewing. To that end the user may select from a plurality of depending members 14 having various widths and lengths so as to best achieve the desired results.

Also contemplated in the invention is the provision of a kit on assemblage that may include the previously described expedients and/or an individually supplied expedient 30 which comprises a plurality of sticker like elements 32 and 34 of various sizes and colors. Thus, depending upon the user's preference and trials, the circular elements 32 of various sizes and colors, as well as opacity may be positioned in the appropriate center of the affected eye lens to block out the distorted image to obtain the desired effect. For aesthetic purposes where sun glasses are utilized a colored partial blocking member may be used.

As seen, the expedient 30 has various sized members to be removed from the wax or release coated backing 36 to be positioned though trial and error, as previously and subsequently described, to obtain the best results.

Example 1

Macular degeneration patient is diagnosed and fitted with prescription glasses and determined to have wet macular degeneration in one eye. Patient is provided with a plurality of circular shaped sticker type partial vision blockers. Patient through trial and error places one of the blockers in the approximate center of lens of the affected eye until the best placement is found with respect to size and location of the partial vision blocker. Through trial and error, a partial vision blocker of various color; opaqueness and size is ultimately selected for best vision results so as to improve overall vision of the patient.

Example 2

Figure 6:
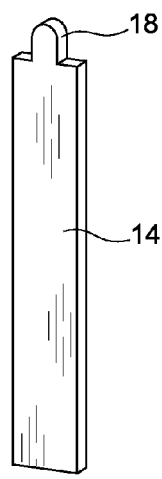
FIG. 6 illustrates one of the partial vision blocking devices of the invention.
Figure 7:
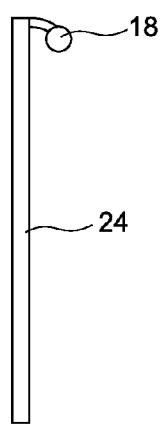
FIG. 7 illustrates another one of the partial vision blocking devices of the invention.

Patient having wet macular degeneration in one eye has a pair of eyeglasses fitted with partial a selected vision blocker holder comprising the device illustrated in FIGS. 2, 3, and 6. Elongated, partial vision blockers of various widths are functionally engaged in releasable fashion in one of the receptacles or notches of the partial vision holder. The partial vision blocker is inserted about midway of the eyeglass lens of the affected eye and through trial and error the best location for the patient is found to provide improved vision results.

Example 3

Patient having macular degeneration in one eye is provided with an eye patch to completely block light and thus images from entering the affected eye which allows for undistorted, unimpaired vision of the uncovered, unaffected eye.

Thus, the method of the invention involves the placement of distorted image blocking members so that the user may have less distorted vision. To achieve the best results, the user would preferably use either of the image blocking means affixed to plain or prescription glasses using a selected distorted image blocking member such as 13, 24, 32, or 34 and orientating the selected distorted image blocking member to achieve the best results through trial and error with the user preferably starting out by central placement of the distorted image blocking member on or adjacent to the affected eye's glass lens, as shown and described. Obviously, synthetic lens materials may also be used, and the image blocking member may be placed on either side of the glasses lens.

The foregoing description of the preferred embodiments of the invention have been presented for the purposes of illustration and description. It is not intended to be exhaustive or to limit the invention to the precise form disclosed. Many modifications and variations are possible in light of the above teachings. It is intended that the scope of the invention not be limited by this detailed description, but by the claims and the equivalents to the claims appended hereto.

What is claimed is:

1. An eye image blocking member adapted for association with a macular degeneration wearer's eyeglasses comprising:
   a) A distorted image blocking element for central placement relative to the lens of said eyeglasses for only blocking the distorted incoming visible light images entering the central portion of the eye of the wearer of said eyeglasses so as to improve eyesight in cases of macular degeneration, which includes a clip member adaptable for association with at least one lens of said wearer's eye glasses for retaining said circular shaped distorted image blocking member in a central portion of said lens.

2. An eye image blocking member adapted for association with a wearer's eyeglasses in accordance with claim 1 wherein said clip member is adapted to releasingly engage said image blocking member.

3. An eye image blocking member adapted for association with a wearer's eyeglasses in accordance with claim 2 wherein said image blocking element is selected from one of a plurality of different sized ones to best block distorted image reception by said wearer.

\* \* \* \* \*